US005462741A

United States Patent [19]

Carr et al.

[11] Patent Number: 5,462,741

[45] Date of Patent: Oct. 31, 1995

[54] HIGH AGENT LOADED CONTROLLED RELEASE DISPENSER

[75] Inventors: John P. Carr, Sunnyvale; Steven D. Larsen, Dublin; James B. Eckenhoff, Los Altos, all of Calif.

[73] Assignee: Alza Corporation, Palo Alto, Calif.

[21] Appl. No.: 234,457

[22] Filed: Apr. 28, 1994

Related U.S. Application Data

[63] Continuation-in-part of Ser. No. 926,614, Aug. 6, 1992, abandoned.

[51] Int. Cl.[6] ........ A61K 9/00

[52] U.S. Cl. ........ 424/438; 424/413

[58] Field of Search ........ 424/438, 473

[56] References Cited

U.S. PATENT DOCUMENTS

| | | | |
|---|---|---|---|
| 3,995,632 | 12/1976 | Nakano et al. | 128/260 |
| 4,111,202 | 9/1978 | Theeuwes | 128/260 |
| 4,251,506 | 2/1981 | Laby | 424/19 |
| 4,595,583 | 6/1986 | Eckenhoff et al. | 424/15 |
| 4,612,008 | 9/1986 | Wong et al. | 604/892 |
| 4,612,186 | 9/1986 | Eckenhoff et al. | 424/15 |
| 4,643,731 | 2/1987 | Eckenhoff | 604/892 |
| 4,717,566 | 1/1988 | Eckenhoff | 424/438 |
| 4,772,474 | 9/1988 | Eckenhoff et al. | 424/465 |
| 4,824,675 | 4/1989 | Wong et al. | 424/438 |
| 4,844,984 | 7/1989 | Eckenhoff et al. | 424/438 |
| 4,855,141 | 8/1989 | Eckenhoff et al. | 424/423 |
| 4,865,598 | 9/1989 | Eckenhoff et al. | 604/892.1 |
| 4,872,873 | 10/1989 | Zingerman | 604/892.1 |
| 4,876,093 | 10/1989 | Theeuwes et al. | 424/438 |
| 4,892,778 | 1/1990 | Theeuwes et al. | 428/218 |
| 4,915,949 | 4/1990 | Wong et al. | 424/438 |
| 4,940,465 | 7/1990 | Theeuwes et al. | 604/892.1 |
| 5,023,088 | 6/1991 | Wong et al. | 424/473 |
| 5,034,229 | 7/1991 | Magruder et al. | 424/422 |
| 5,045,082 | 9/1991 | Ayer et al. | 604/892.1 |
| 5,122,128 | 6/1992 | Cardinal et al. | 604/890.1 |
| 5,126,142 | 6/1992 | Ayer et al. | 424/473 |

FOREIGN PATENT DOCUMENTS

| | | | |
|---|---|---|---|
| 0025699 | 3/1981 | European Pat. Off. | A61D 7/00 |
| 0164241 | 5/1987 | European Pat. Off. | A61K 9/22 |

OTHER PUBLICATIONS

Grafton, P., "General Principles for Designing with Plastics," 1969–1970 Modern Plastics Encyclopedia pp. 62 to 71.

Wurster, Dale E. "Air–Suspension Technique of Coating Drug Particles," J. of Amer, Phar Assoc. vol. XLVIII, No. 8. pp. 451 to 454, 1959.

Wurster, Dale E., "Preparation of Compressed Tablet Granulations by the Air–Suspension Technique II," pp. 82 to 84, J. of Amer. Phar. V. 49, No. 2.

Felmeister, Alvin, "Powders," pp. 1626–1680, Remington's 14th Ed. 1970, Mack Publishing Co.

*Primary Examiner*—D. Gabrielle Phelan

*Attorney, Agent, or Firm*—Paul L. Sabatine; Felissa H. Cagan; Richard T. Ito

[57] ABSTRACT

A fluid-activated delivery device is disclosed comprising a housing defining an internal compartment, a beneficial agent formulation in the compartment, exit means in the housing for delivering the beneficial agent formulation from the delivery device, and wherein the formulation comprises an active agent in an amount of 50 wt % or greater blended with a glyceride or a mixture of glycerides of a fatty acid.

15 Claims, 4 Drawing Sheets

HIGH AGENT LOADED CONTROLLED RELEASE DISPENSER

CROSS-REFERENCE TO RELATED APPLICATION

This application is a continuation-in-part of U.S. Ser. No. 07/926,614 filed Aug. 6, 1992, now abandoned which application is incorporated herein and benefit is claimed of its filing date.

DESCRIPTION OF TECHNICAL FIELD

This invention pertains to the delivery of a beneficial agent to an animal. More particularly, the invention is concerned with the controlled administration of an agent, preferably a drug, to an animal over a prolonged period of time, where the delivery device comprises a high loading concentration of agent.

DESCRIPTION OF BACKGROUND OF THE INVENTION

Delivery devices for administering a beneficial agent to a biological environment comprising a fluid are known in the prior art. Representative examples of delivery devices are disclosed in European publications EP 25,699 and 164,241; and in U.S. Pat. Nos. 3,995,632; 4,111,202; 4,251,506; 4,612,008; 4,824,675; 4,865,598; 4,872,873; 4,876,093; 4,892,778; 4,915,949; 4,940,465; and 5,023,088.

While the prior art delivery devices usually work successfully for their intended purpose, the present inventors observed that the devices often do not function well when the dispensed formulation is combined with a carrier. When a formulation agent is dispensed from the previous devices, uncontrolled and nonuniform release of the agent is often a problem over prolonged dispensing periods, causing delivery of the agent into the environment of use in amounts and over periods of time that are not intended by the design of the prior art device, which results in erratic or incorrect dosage profiles. This has been found to be particularly true in dynamic or vigorous environments such as active, grazing animals. An additional drawback to the prior art formulations is that they attract fluid and in fact require some fluid for proper dissemination of agent into the environment and also for lubrication within the device. This presents a problem when the beneficial agent is sensitive to fluids and subject to degradation or inactivation in an aqueous environment.

Devices have been designed which contain beneficial agents in carriers, for example in U.S. Pat. No. 4,595,583. While these devices appear to solve the problem of excessive and uncontrolled erosion of the agent formulation, they have a low loading of agent within the formulation, usually of less than 40% and often lower, of 30% or less. This creates a serious problem in those instances when it is desired to have agent delivered from a single device over a period of several weeks or months, as is the case with implants and ruminal boluses. The amount of beneficial agent necessary to be included in the device for such an extended delivery period would require a very large amount of formulation at a low dosing, making the device far too large and bulky to be useful as a practical matter as an implant or ruminal bolus, for example.

One group of beneficial agents that requires special delivery technology are the ionophores. Ionophores, or ion-bearers, as reported in Ann.N.Y.Acad.Sci., Vol. 264, pp 373–86 (1985), are polyether antibiotics that modulate the physiological transport of ions across biological membranes and alter the characteristics of fermentation in the animal, resulting in favorable metabolic changes. These valuable properties of ionophores led to their use as feed additives by the livestock industry. For example, the ionophores, when fed to ruminants, resulted in an improved feed-gain ratio, as reported in Feedstuffs, pp 14, 15 and 22 (1989). In one accepted use, ionophores are fed to feedlot cattle in confinement for improved feed efficiency. In this use, the ionophore first is mixed with a finely ground nonmedicated feedstuff to produce a premix, which premix is added to an air-dry feed for feeding to cattle, including steers and heifers.

While the above described prior art use of ionophores results in improved feed efficiency, usually of from 5 to 8 percent or higher, for steers and heifers, as reported in Feedstuffs (supra), serious shortcomings accompany this use. For example, since the ionophore is mixed with feed, one shortcoming is the difficulty to ascertain the amount of ionophore ingested by the animal because of feedlot losses such as spillage and scatter. Another shortcoming resides in the absence of controlled administration of known amounts of the ionophore over time, as the composition of the feed charged with the ionophore can vary with feed millers. Also, ionophores are sensitive to moisture in the environment, which moisture can adversely affect their usefulness, and the handling and transport of feeds containing ionophores can result in the segregation of particles carrying ionophores and change the concentration level to which cattle are exposed when fed over time. Then, since ionophores usually are mixed with feeds daily, this requires extra labor that adds to the cost of the ionophore-feedstuff.

In the light of the above presentation, it will be appreciated by those versed in the dispensing art to which this invention pertains that a pressing need exists for a dosage form that can deliver a beneficial agent, such as the ionophores, to a biological environment of use in large amounts in a small volume. The pressing need exists also for a dosage form that can store a beneficial agent in a carrier and deliver the beneficial agent and carrier at a controlled rate in a substantially constant dose per unit time over a prolonged period of time essentially independent of the environment of use. It will be appreciated further by those versed in the dispensing art that if such a novel and unique dosage form is provided that can administer a beneficial agent in a carrier at a high loading and in a rate-controlled dose over time and, simultaneously, provide the beneficial effects, the dosage form would represent an advancement and valuable contribution in the agent dosage form art.

SUMMARY OF THE INVENTION

The present invention is directed to an improvement in a delivery device that is fluid-activated, wherein the delivery device comprises a housing defining an internal compartment, a thermo-responsive beneficial agent formulation in the compartment, exit means in the housing for delivering the beneficial agent formulation from the delivery device, a fluid-activated expandable driving member in the compartment, optionally a partition layer between the beneficial agent formulation and the driving member, and optionally a density element in the compartment; wherein the improvement comprises a thermo-responsive beneficial agent formulation comprising an active agent in an amount of 45 wt % (percent by weight) or greater in a carrier such as a responsive monoglyceride or mixture of monoglycerides of fatty acids.

DETAILED DESCRIPTION OF THE INVENTION AND PREFERRED EMBODIMENTS

Figure 1:
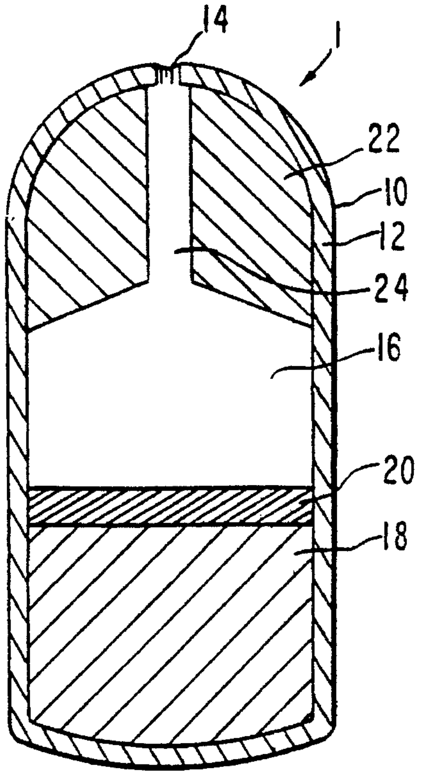
FIG. 1 is a cross-sectional view of one embodiment of a delivery device according to the present invention.

It has now been discovered by the inventors that it is possible for certain beneficial agents to be incorporated in certain thermo-responsive monoglycerides of fatty acids in a super-saturated state. The monoglyceride carrier vehicle suspends and partially solubilizes the agent. This allows the agent to be present in the carrier material at a high agent loading, that is, in an amount of 50 wt % or greater. This high loading provides the advantage of obtaining a maximum amount of agent in a minimum amount of carrier to give fluid-activated osmotic delivery devices of a small size that are convenient for use as implants or ruminal boluses in animals, including humans, for the long-term delivery of agent over a prolonged period of time.

The "prolonged" delivery of agent refers to delivery of beneficial agent which continues for a period of time of 1 to 25 days or longer, generally 1¼ to 60 days or longer, and more generally 120 days or longer.

The term "agent" as used herein describes any beneficial agent or compound that can be delivered by a device according to this invention to produce a beneficial or useful, including a therapeutic, result. The term includes medicines or drugs, such as inorganic or organic drugs, anthelmintics, antiparasitic agents, antimicrobial agents, sulfa drugs, anti-flea agents, rumen fermentation manipulators and ionophores, minerals and mineral salts such as selenium, anti-bloat agents, growth supplements, vitamins, antienteritis agents, nutritional supplements, hormones and hormonal agents, proteins and peptides, and the like. It is to be understood that more than one beneficial agent may be incorporated into the beneficial agent formulation in a device of this invention, and that the use of the term "agent" in no way excludes the use of two or more such agents. The terms "beneficial agent", "agent" and "drug" are used interchangeably herein.

The agents or drugs can be in various forms, such as uncharged molecules, molecular complexes, and pharmacologically acceptable salts. Derivatives of compounds, such as esters, ethers, amides, and the like, can be used. The amount of agent or drug present in a device generally can be from about 5 mg to 10 g. The devices of the invention can dispense from 0.1 to 50 mg/hr.

In a presently preferred embodiment of the present invention, the beneficial agent is an ionophore. Beneficial ionophores that can be dispensed using the dosage form of this invention comprise natural and synthetic ionophores. The ionophores are polyethers and they possess the ability to transport mono- and divalent cations across lipid bilayers which lie within biological membranes. The ionophores possess unique properties which derive from their ability to perturb transmembrane ion gradients and electrical potentials. The ability of ionophores to complex and transport ions leads to their applications as antibiotics against gram-positive microorganisms, against mycobacteria, as growth promotants in ruminants such as cattle and sheep, and for improved feed utilization as seen by increasing the efficiency of meat production. Ionophores that can be stored and dispensed by the dosage form of this invention comprise a member selected from the group consisting of azolomycin, valinomycin, enniactin, monactin, nonactin, dinactin, trinactin, virginiamycin, tetronasin, rumensin, semduramicin, monensin, monensin sodium, monensin factor B, monensin factor C, nigericin, narasin also known as methyl salinomycin, salinomycin, enitabas, isolasalocid, lasalocid, lysocellin, septamycin, laidlomycin, laidlomycin propionate, laidlomycin butyrate, Ionomycin, lenotemycin, grisorixin, ferensimycin, alborixin, rosgramicin, erythromycin, sodium lysocellin, and the like. The polyethers include bambermycin, monenomycin, flavomycin, and the like. The ionophores also comprise the pharmaceutically acceptable derivatives having ionophore activities, such as the pharmaceutically acceptable salts, the alkyl and alkenyl derivatives, the monoglycoside and diglycoside derivatives, the hydroxylated derivatives, the free acid, the hydrate, the ester derivatives, the ether derivatives, and the like. In one presently preferred embodiment, the ionophores exhibit a molecular weight of about 350 to 2500. The ionophores are known in the ionophore art in "Kirk-OthmerEncyclopedia", Vol. 3, pp 47–64 (1978); Ann.N.Y.Acad.Sci., Vol. 264, pp 373–86 (1975); and ACSSym., Ser. 140, pp 1–22 (1980). The ionophore can be present as a base, as a salt, as an ester, or as another derivative thereof. The beneficial agent is present in the invention in a therapeutically effective amount; that is, in an amount that is necessary to provide a desired therapeutic, beneficial, effect. The presently preferred amount of a beneficial agent in the beneficial agent formulation is at least 50 wt %, and can be 70 wt % or greater.

The thermo-responsive carrier forming, together with the beneficial agent, the beneficial agent formulation of this invention is selected from those thermo-responsive materials which are preferably hydrophobic and which allow for the beneficial agent to be suspended and partially dissolved in the carrier in high amounts to provide a loading of the agent of 50 wt % or greater. The high loading dose of beneficial agent in a carrier is effected according to the mode and the manner of the invention by first heating the beneficial agent followed by heating the carrier and then adding the preheated beneficial agent to the heated carrier. The high loading dose of beneficial agent in a carrier is effected also according to the mode and the manner of the invention by simultaneously heating the beneficial agent and the carrier in contacting layered arrangement followed by blending into a beneficial agent carrier mass. The term "thermo-responsive" as used for purposes of this invention refers to heat-sensitive materials that are capable of softening or becoming dispensable in response to heat and hardening again when cooled. The term "thermo-responsive" in a preferred embodiment denotes the physical-chemical property of a composition agent carrier to exhibit solid or solid-like properties at temperatures of up to about 31° C., and become fluid, semisolid or viscous when disturbed by heat at temperatures from 31° C., usually in the range of about 31° C. to about 45°

C. The thermo-responsive carrier has the property of melting, dissolving, undergoing dissolution, softening or liquefying at the elevated temperatures, thereby making it possible for the delivery device of the present invention to delivery the thermo-responsive carrier with the beneficial agent homogeneously or heterogeneously blended therein. Thermo-responsive carriers are discussed generally in U.S. Pat. No. 4,595,583. Another important property of the carrier is its ability to maintain the stability of the beneficial agent therein during storage and delivery of the agent to the environment of use.

It has now been found that a particular class of thermo-responsive carriers has the particularly desired characteristic of containing a beneficial agent, and particularly ionophores, in a super-saturated state for providing a very high loading of the agent, of from 50 wt % up to 70 wt % and greater. This class encompasses the monoglycerides of fatty acids. As used herein, the term "monoglyceride" refers to a monoglyceride or a mixture of monoglycerides of fatty acids with a total monoesters content of at least 51%. Typically, monoglyceride has been available as a mixture of monoglycerides of fatty acids, with one monoglyceride being the principal component. One example of commercially available monoglyceride is Emerest® 2421 (Emery Division, Quantum Chemical Corp.), which is a mixture of glycerol oleates with a glycerol moniliid content of 58% and a total monoesters content of 58%. Another example are the distilled monoglycerides under the name Myverol® (Eastman Chemical Products), examples of which are Myverol® 18–99, having a glycerol moniliid content of 61% and a total monoesters content of 93%; Myverol® 18–92, having a glycerol monolinoleate content of 68%, a glycerol moniliid content of 21%, and a minimum total monoesters content of 90%; Myverol® 18–50, having a glycerol monolinoleate content of 49%, a glycerol moniliid content of 26%, and a total monoesters content of 90%; and Myverol® 18–30, having a glycerol moniliid content of 40%, a glycerol monopalmitate content of 28%, a glycerol monostearate content of 23%, and a total monoesters content of 90%. The fatty acids have from 4 to 26 carbon atoms and may be saturated or unsaturated and straight chained, and include, for example, lauric acid, myristic acid, stearic acid, oleic acid, linoleic acid and palmitic acid. Preferred monoglycerides for use in the present invention are those which have a melting point below 69° C., as it has been found that with those having melting points of about 69° C. or above, while incorporation of beneficial agent into the monoglyceride material in high amounts was easily obtained, the resulting agent formulation did not soften sufficiently at 40° C. to be delivered from a delivery device of this invention. In addition, monoglyceride carrier materials were found to protect fluid-sensitive beneficial agents from degradation by hydrolysis upon exposure to water and to disperse satisfactorily within aqueous media after delivery from the device. While the presentation discloses monoglycerides, the invention embraces additionally diglycerides and triglycerides.

Turning now to the drawing figures in detail, which are not to scale but are provided for means of illustration, FIG. 1 is an opened view of delivery device or dispenser 1, which depicts a ruminal bolus. Device 1 comprises a housing 10, defined by a wall 12 which surrounds an internal compartment or lumen, and exit means 14. Wall 12 comprises, in a presently preferred embodiment, a semipermeable wall-forming composition that is substantially permeable to the passage of an external fluid and substantially impermeable to the passage of a beneficial agent and other ingredients contained in the delivery device 1. In another embodiment, wall 12 can be formed of a semipermeable composition in a portion in contact with a fluid-activated driving means, with the remainder of wall 12 comprising a different wall-forming composition that is impermeable to fluid. Materials which are appropriate for use in forming the wall are known to the art and are set forth, for example, in U.S. Pat. No. 4,772,474. Wall 12 is non-toxic, it is inert, and it maintains its physical and chemical integrity, that is, it does not erode during the dispensing period. The internal compartment formed by wall 12 contains a thermo-responsive beneficial agent formulation 16 comprising a beneficial agent mixed homogeneously or heterogeneously with a hydrophobic thermo-responsive carrier composition, and a fluid-activated expandable driving means or member 18 that is separated from thermo-responsive beneficial agent formulation 16 by moveable partition layer 20. The expandable driving member 18 is positioned opposite exit means 14, with beneficial agent formulation 16 positioned between them. The driving member 18 usually comprises a hydrogel composition which includes a swellable, expandable polymer and, optionally, an osmotically effective solute. The driving member provides a driving source for delivering the beneficial agent formulation from the compartment to the environment of use via the exit means 14. Materials which are appropriate for use in forming expandable driving members are known in the art and are described in, for example, U.S. Pat. No. 4,772,474. Partition layer 20 is positioned between the agent formulation 16 and the driving member 18 for substantially maintaining the separate identity of the beneficial agent formulation and the expandable driving member. Such an embodiment is further described in U.S. Pat. Nos. 4,772,474 and 4,844,984. In an alternative embodiment (not shown), partition layer 20 is not present in the device. Also contained within the internal compartment is density means or densifier 22 which is positioned distant from expandable driving member 18. Density member 22 has a bore 24 therethrough for dispensing the beneficial agent formulation 16 from the internal compartment through exit means 14 for release from delivery device 1. Density member 22 is dense enough to retain the dispensing device in the environment of use. When the environment of use is the rumen of a ruminant, the density member is a necessary element of the dispensing device. Density members are known in the art, and appropriate members are shown and described in U.S. Pat. Nos. 4,643,731 and 4,772,474.

In another embodiment of the device of the present invention, a screen or insert (not shown) having a grid-like series of openings is present in the orifice of exit means 14 adjacent the outside environment of use for preventing blockage of the orifice by exogenous materials and for otherwise improving the performance of the device. Such screens and inserts are described in U.S. Pat. Nos. 4,872,873 and 5,122,128.

Figure 2:
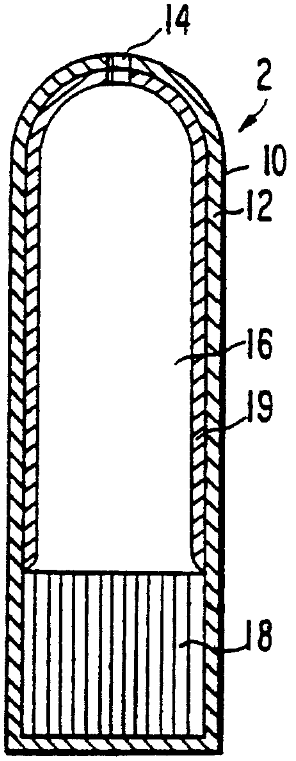
FIG. 2 is a cross-sectional view of another embodiment of a delivery device according to the present invention.

FIG. 2 illustrates a delivery device 2 of the present invention, depicting an implant. Delivery device 2 comprises housing 10, semipermeable wall 12 surrounding an internal compartment, exit means 14, thermo-responsive hydrophobic beneficial agent formulation 16, and expandable driving member 18. Beneficial agent formulation 16 and driving member 18 are in layered contact through a contacting surface of each composition. Additionally, the internal compartment of device 2 also contains impermeable layer 19 for substantially protecting a beneficial agent that is sensitive to fluid from an exterior fluid present in the environment of use. Layer 19 comprises a material that is substantially impermeable to the passage of fluid and it prevents fluid that has passed through wall 12 from entering the internal compartment in the region protected by layer 19. Layer 19 in the embodiment illustrated is in contact with the internal surface of wall 12. Layer 19 is designed and adapted, in one embodiment, as a sleeve or an internal liner and it contacts and covers the internal surface area occupied initially by the beneficial agent formulation 16. In another embodiment, layer 19 is a coating applied as a coat on the internal surface of wall 12 to cover the internal surface area initially occupied by the beneficial agent formulation. Compositions suitable for layer 19 and suitable embodiments and materials therefor are disclosed in U.S. Pat. No. 4,855,141. In an alternative embodiment (not shown), impermeable layer 19 is not present in the device.

Another embodiment of a device which may be used as an implant with the present invention is disclosed in U.S. Pat. No. 5,034,229. This device has an impermeable wall portion surrounding the beneficial agent formulation and a semipermeable wall portion surrounding the expandable driving member. Such a device provides protection to beneficial agents that are sensitive to fluids.

The dispensing device of this invention, when in operation, delivers beneficial agent formulation 16 to an animal fluid environment of use by a combination of thermodynamic and kinetic integrally performed activities. That is, in operation, the heat-sensitive, thermo-responsive carrier in formulation 16 in response to the body temperature of an animal recipient absorbs thermal energy and melts or softens or undergoes dissolution or forms a semipaste-like composition for delivering the beneficial agent through exit means 14. As formulation 16 absorbs thermal energy and undergoes change, concomitantly external fluid enters the delivery device through a fluid-permeable component of wall 12 and is absorbed or imbibed by expandable driving member 18 to continuously expand and swell, causing it to increase in volume. As the expanding driving member 18 occupies space in the internal compartment of the device, it moves against or it urges partition layer 20 to move against beneficial agent formulation 16 to push the formulation through exit means 14 to the exterior of the delivery device.

The delivery device of the invention can be sized and shaped for administering a beneficial agent to a variety of animals. In a presently preferred embodiment, the delivery device can be adapted for delivering an ionophore or other beneficial agent to ruminant animals including cattle, sheep, giraffes, deer, goats, bison and camels, and more particularly cattle and sheep, that comprise an important group of animals that require periodic administration of various agents. The delivery device can embrace a capsule-like shape and in one design have a diameter of from about 0.5 inches to about 1 inch (about 1.3 cm to about 2.5 cm) and a length of from about 0.5 inches to about 2.5 inches (about 1.3 cm to about 6.6 cm). For use with cattle, the delivery device has a diameter of from about 0.5 inches to about 1.5 inches (about 1.3 cm to about 3.8 cm), and a length of from about 1 inch to about 5 inches (about 2.5 cm to about 12.7 cm).

While FIGS. 1 and 2 illustrate various dosage forms that can be made according to the invention, it is to be understood that these dosage forms are not to be construed as limiting the invention, as the delivery device can take other shapes, sizes and forms for delivering a beneficial agent to a biological environment of use. The delivery device may be used to deliver an agent to animals including warm-blooded animals, mammals and humans. The delivery device can be used in hospitals, clinics, nursing homes, veterinary clinics, farms, zoos, laboratories, on the range, in feed lots, and other environments of use. The delivery device can be used for dispensing a beneficial agent formulation to a fluid environment of use, wherein the fluid environment is an aqueous environment, which aqueous environment includes biological aqueous-type fluids. The presently preferred environment of use comprises the rumen of a ruminant animal. However, the devices are not restricted to use in ruminant animals or to a rumen environment of use. The environment of use can comprise a body cavity such as the peritoneum, vagina, or intestinal tract. The device may also be utilized as a subcutaneous implant. A single dispensing device or several dispensing devices can be administered to a subject during a therapeutic program.

In an embodiment of the invention, the beneficial agent and the carrier are heated separately to a temperature approximating the melting temperature, or to a temperature less than the temperature of degradation, usually the melting point temperature, prior to adding the beneficial agent to the carrier. One procedure is disclosed in AnnualBookofASTMStandards, pp 376 to 378, 1993; and in GuidelinesForTestingofChemicals, pp 1 to 13, 1981. The melting point determines the temperature at which a beneficial agent, or the carrier changes its physical state from solid to a liquid. Test methods, disclosed in the cited reference, such as capillary method, metal block, photocell detection, Kofler hot bar, and melt microscope can be used for this purpose.

The wall of a device can be formed by molding, air spraying, dipping, compressing or brushing with a wall forming composition. Other and preferred techniques that can be used for applying wall forming materials are the air suspension procedure and the pan coating procedure. The air procedure consists in suspending and tumbling the device forming materials in a current of air and a wall forming composition until the wall surrounds and coats a core. The procedure can be repeated with different wall forming compositions. The air suspension procedure is described in U.S. Pat. No. 2,799,241; J.Am.Pharm.Assoc., Vol. 48, pp 451 to 459 (1959) and ibid., Vol. 49, pp 82 to 84 (1960). Other standard manufacturing procedures are disclosed in ModernPlasticEncyclopedia, Vol. 46, pp 62 to 70 (1969); and in PharmaceuticalSciences, by Remington, 14th Ed., pp 1626 to 1678 (1970); published by Mack Publishing Co., Zastin, Pa.

The expression exit means comprise "means for releasing beneficial agent" includes passageway, aperture, bore, pore, porous element through which the beneficial agent can migrate, hollow fiber, capillary tube, microporous member, and the like. The means for releasing agent include a material that is removed from the wall during use such as eroding in the environment of use to produce at least one passageway in the device. Representative materials suitable for forming a passageway include erodible poly(glycolic), poly(lactic)in the wall, gelatinous filaments, poly(vinyl alcohol), and the like. The passageway can be formed by leaching a material such as sorbitol from the wall. The passageway can have any shape such as round, triangular, square, elliptical, irregular, and the like. The device can be constructed with more than one passageway, especially for dispensing released agent over a wide area. In a preferred embodiment, when the device is fabricated with more than one passageway, they can be constructed as the functional equivalent of a single passageway. The passageway can be formed also by mechanical drilling or laser drilling through the wall. A description of means for releasing a beneficial agent as described herein is disclosed in U.S. Pat. Nos. 3,845,770 and 3,906,899. Procedures for forming at least one passageway of governed porosity by leaching from a wall, such as a cellulose wall, a pore former is disclosed in U.S. Pat. Nos. 4,200,098; 4,235,236; 4,309,996, and 4,320,759. The leaching or dissolving of a pore former from a wall forming material is known also in U.S. Pat. Nos. 4,256,108; 4,265,874 and 4,344,929. Laser drilling equipment having photo detection means for orienting a device for selecting a surface for drilling a passageway for communicating with a preselected area inside a device is known in U.S. Pat. Nos. 4,063,064 and 4,008,864.

Exemplary solvents suitable for manufacturing the walls include inert inorganic and organic solvents that do not adversely harm the materials, the wall, the beneficial agent, the thermo-responsive composition, the expandable member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, n-gutyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the wall is applied at a temperature a few degrees less than the melting point of the thermoresponsive composition. Or, the thermoplastic composition can be loaded into the dispenser after applying the wall.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

Formulations comprising laidlomycin propionate and monoglycerides having different melting points were prepared as follows:

The monoglyceride (20 wt %) was heated to approx. 92° C. and the potassium salt of laidlomycin propionate (80 wt %) was then mixed in thoroughly. The mixture formed a continuous paste at 92° C. The paste hardened when cooled to room temperature. The following formulations, all containing 80 wt % laidlomycin propionate (as the potassium salt), were prepared in this manner.

TABLE A

| Formulation | Monoglyceride | Melting Point |
|---|---|---|
| A | Myverol 18-50 | 54° C. |
| B | Myverol 18-92 | 41° C. |
| C | Myverol 18-06 | 69° C. |

A formulation (Formulation D) of 80 wt % potassium salt of laidlomycin propionate and 20 wt % Myvaplex® 600 (concentrated glycerol monostearate, 69° C. melting point; Eastman Chemical) was also prepared, following the above procedures.

EXAMPLE 2

The above formulations were incorporated into delivery devices according to this invention and were then tested for flowability from the devices in vitro, as follows.

The delivery device was manufactured by first preparing the semipermeable wall. 79.0 Grams cellulose acetate butyrate, having a butyryl content of 37% and an acetyl content of 13% (Eastman Chemical), was sized and combined with 15.0 g Citroflex-2® (triethyl citrate, Pfizer Inc.) and 6.0 g polyethylene glycol having a molecular weight of 400 (PEG 400, Union Carbide). The mixture was stirred together for 20 min., after which the material was transferred to the feed hopper of an injector molder equipped with a suitable mold to produce a cellulosic cup weighing 10.1 g and having the following dimensions: 7.9 cm height, 2.5 cm width and wall thickness of 0.17 cm.

To prepare the expandable driving member, a blend of 60.3 g cellulose gum (sodium carboxymethylcellulose 7H4F, Hercules Co.), 0.9 g polyvinylpyrrolidone (PVP), 0.9 g magnesium stearate, 12.9 g water and 25 g sodium chloride was made. 9.1 Grams of the blend was compressed to form a tablet conforming to the internal shape of the semipermeable cellulosic cups described above and having a height of 0.74 in. (1.88 cm). One compressed hydrophilic expandable driving member tablet was then inserted into the cup.

One of the formulations from Example 1 was heated until melted and then 20.0 g (about 20.0 mL) was delivered to a prepared cup assembly. The formulation was then allowed to cool and solidify to form an interface adjacent with the expandable driving member.

A sintered iron densifier having a 0.5 in. (1.3 cm) bore axially therethrough was inserted into the open end of the cup assembly. The densifier was seated against the beneficial agent formulation. The protruding lip of the cup was heated until softened using a hot air gun, and the lip was crimped over the densifier to make a completed delivery device.

The completed devices were placed in deionized water and held at 40° C. for six weeks. The devices were observed visually during that period of time. The results showed that Formulations A and B were sufficiently softened and flowable at 40° C. for delivery of each formulation from the device, whereas Formulations C and D were too viscous at 40° C. for acceptable delivery.

EXAMPLE 3

Figure 3:
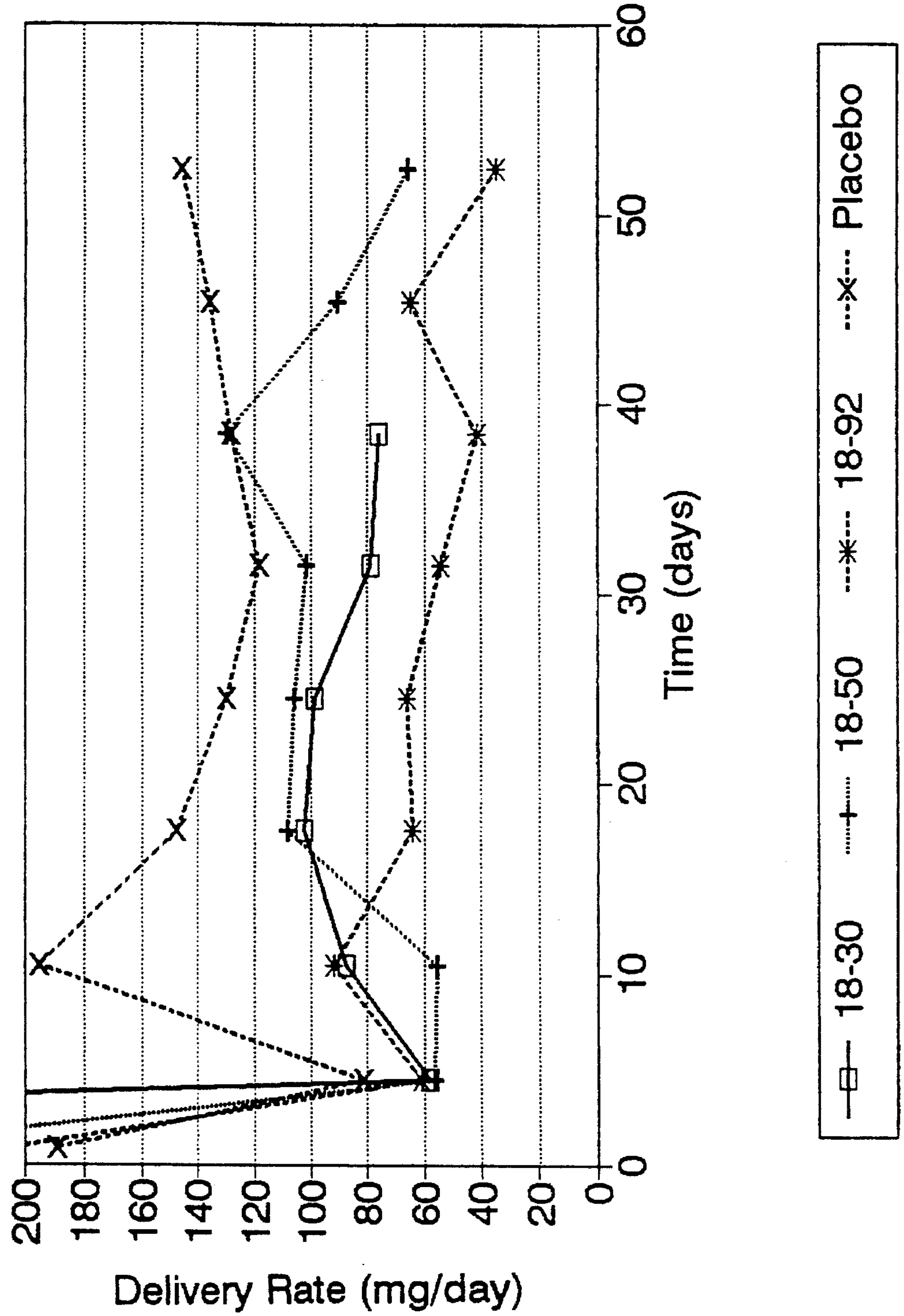
FIG. 3 is a graph showing the average in vitro release rate over time of laidlomycin propionate formulations from delivery devices according to the present invention.

Following the procedures of Example 2 for testing release in vitro, the release rate of laidlomycin propionate from devices of the invention over an extended period of time was tested. Devices were prepared as in Example 2 and containing either Formulation A, Formulation B, Formulation E (80 wt % potassium salt of laidlomycin propionate in 20 wt % Myverol 18–30, m.p. 60° C.) or a placebo (100% Myverol 18–50). Devices with Formulations A and E and the placebo formulation had a 0.35 inch (0.9 cm) bore through the densifier, and devices with formulation B had a 0.20 inch (0.5 cm) bore through the densifier. The devices were held in deionized water at 40° C. At intervals of seven days, the devices were removed to new deionized water, and the previous deionized water was evaporated away and the residual drug formulation was measured gravimetrically to determine the amount released into the aqueous environment. The results are presented in FIG. 3.

EXAMPLE 4

Figure 4:
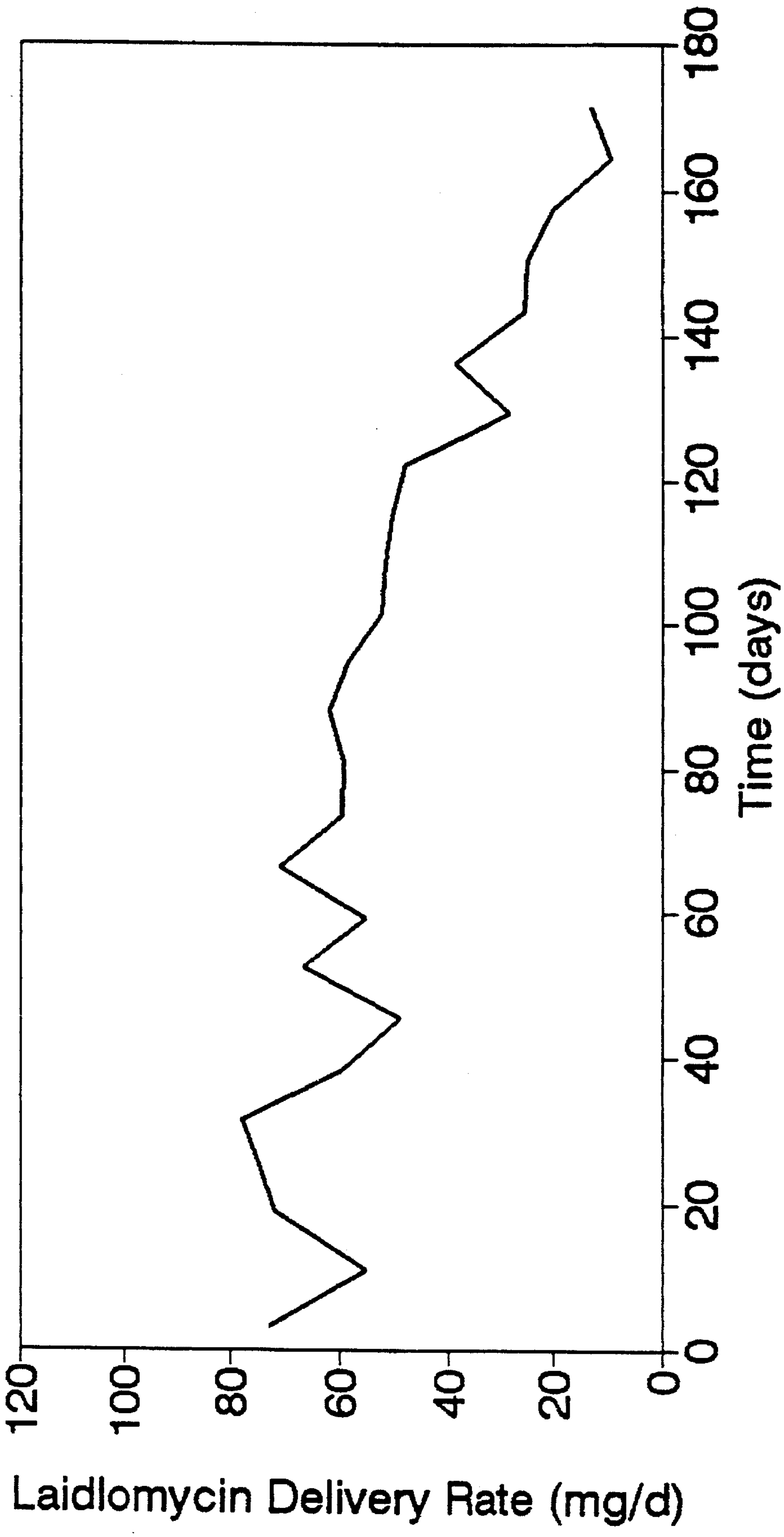
FIG. 4 is a graph showing the average in vitro release rate over time of a laidlomycin propionate formulation from a delivery device according to the present invention.

Devices were prepared as in Example 2 containing Formulation A and having a semipermeable membrane composed of 75 wt % cellulose acetate butyrate (37% butyryl content and 13% acetyl content), 12 wt % Citroflex-2®, and 12 wt % polyethylene glycol (PEG 400). Following the procedures of Example 3 for testing release in vitro, the extended release rate of six devices over a six month period was tested. The results (average of six devices) are presented in FIG. 4.

EXAMPLE 5

Figure 5:
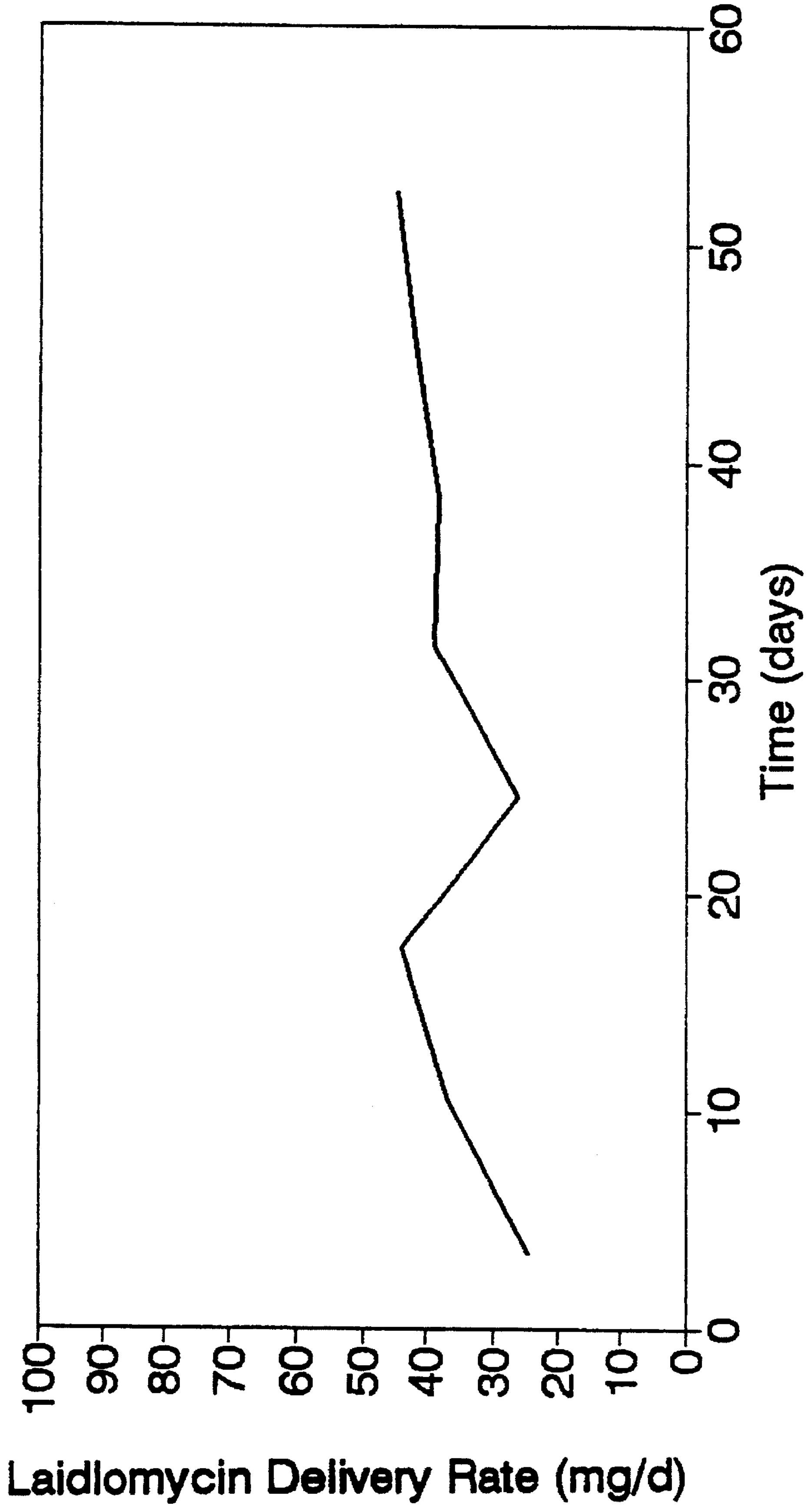
FIG. 5 is a graph showing the average in vitro release rate over time of a laidlomycin propionate formulation from a delivery device according to the present invention.

Devices were prepared as in Example 2 and containing a formulation composed of 70 wt % potassium salt of laidlomycin propionate and 30 wt % Myverol® 18–50 monoglyceride and a semipermeable membrane composed of 80 wt % cellulose acetate butyrate (37% butyryl content and 13% acetyl content), 8 wt % Citroflex-4® (tributyl citrate, Morflex Inc.), and 12 wt % polyethylene glycol (PEG 400). Following the procedures of Example 3 for testing release in vitro, the extended release rate of six devices over a two month period was measured. The results (average of six devices) are presented in FIG. 5.

EXAMPLE 6

A beneficial agent carrier composition for delivery from a controlled delivery device is prepared as follows: first, 10 g of a monoglyceride is placed into a glass beaker and then overlayed with 40 g of potassium laidlomycin propionate, the unstirred beaker covered with foil and placed in a forced air oven preheated to 80° C. to simultaneously heat the monoglyceride and the beneficial agent laidlomycin. The beaker is held in the oven for 35 minutes with concomitant melting of the two components, which were stirred to intermix the beneficial agent and the carrier. The beaker is returned to the oven for an additional 45 minutes, after which the mixture is stirred again to assure homogeneity. The mixture formed a continuous paste at 80° C., which paste hardened on cooling to 25° C. The final composition comprises 80 wt % potassium laidlomycin propionate and 20 wt % monoglyceride.

EXAMPLE 7

The procedure of Example 6 is followed in this example, with conditions as described except the present example comprises a member selected from the group consisting of a monoglyceride, a diglyceride and a triglyceride comprising one, two or three molecules of a fatty acid esterified with a mole of glycerol. The fatty acid comprises a saturated fatty acid of $C_4$ to $C_{26}$ and an unsaturated fatty acid of $C_{10}$ to $C_{24}$ carbons. Examples of saturated fatty acids are caproic, caprylic, lauric, palmitic, and stearic, and representative of unsaturated fatty acids include oleic, linoleic, linolenic and arachidonic.

EXAMPLE 8

A beneficial agent-carrier composition is prepared as follows: first, 20 g of sodium lysocellin is heated to 40° C., and the mixture then placed in an oven for 40 minutes at 75° C., Next, the triglyceride and the ionophore are stirred to yield a mixture, after which the mixture is heated for 35 minutes in the oven to produce a homogenous composition comprising 80 wt % sodium lysocellin and 20 wt % glyceryl tristearate.

EXAMPLE 9

The procedure of Example 8 is followed, except in this example the glyceride is a member selected from the group consisting of glyceryl trioleate, glyceryl tripalmitate, glyceryl tristearate, glyceryl trilinoleicate, glyceryl dilauricate, glyceryl dicaprylicate, glyceryl monoceroticate, and the ionophore is a member selected from the group consisting of azolomycin, valinomycin, enniactin, monactin, rumensin, salinomycin, and ferensimycin.

EXAMPLE 10

The invention pertains also to a method for delivering the maximum dose of an ionophore to a patient in need of an ionophore, wherein the method the steps of: (A) admitting orally into the patient a delivery system comprising: (1) a semipermeable wall that surrounds a (2) composition comprising 50 wt % to 80 wt % of an ionophore and 20 wt % to 50 wt % of a mono, di, or triglyceride, (3) exit means in the wall for delivering the composition from the delivery system; (B) imbibing fluid through the wall into the delivery system causing the composition to be hydroactive, thereby; (C) delivering the composition to the patient; and, wherein the composition is characterized by heating the before blending with the glyceride to provide the composition delivered by the delivery system.

Inasmuch as the foregoing specification comprises many embodiments of the invention, it is understood that variations and modifications may be made herein in accordance with the inventive principles disclosed, without departing from the scope of the invention.

We claim:

1. A delivery system comprising: a housing pervious to fluid; a composition comprising 50 wt % to 80 wt % of a beneficial agent and 20 wt % to 50 wt % of a glyceride; and, exit means in the housing for releasing the composition from the delivery system; and wherein the composition is characterized by: the beneficial agent is heated to a temperature approximately its melting temperature prior to blending with the glyceride heated to temperature approximating its melting temperature to provide the composition in the delivery system.

2. The delivery system according to claim 1, wherein the beneficial agent is an ionophore.

3. The delivery system according to claim 1, wherein the beneficial agent is a member selected from the group consisting of azolomycin, valinomycin, enniactin, monactin, nonactin, dinactin, trinactin, virginiamycin, tetronasin, rumensin, semduramicin, monensin, nigericin, narasin, salinomycin, isolasalocid, lasalocid, lysocellin, septamycin, laidlomycin, Ionomycin, lenotemycin, grisorixin, ferensimycin, alborixin, rosgramicin, erythromycin, lysocellin, bambermycin, monenomycin, and flavomycin.

4. The delivery system according to claim 1, wherein the glyceride is a member selected from the group consisting of a monoglyceride, diglyceride and triglyceride.

5. The delivery system according to claim 1, wherein the glyceride comprises a saturated fatty acid selected from the group consisting of butyric, isovaleric, caproic, caprylic, capric, lauric, myristic, palmitic, stearic, arachidic, behenic, lignoceric, and cerotic acid.

6. The delivery system according to claim 1, wherein the glyceride comprises an unsaturated fatty acid selected from the group consisting of decylenic, dodecylenic, palmitoleic, oleic, vicinoleic, petroselinic, vaccenic, linoleic, linolenic, eleostearic, licanic, parinaric, tariric, gadoleic, arachidonic, cetoleic, erucic, and nervonic acid.

7. A delivery system comprising: a housing pervious to fluid; a composition comprising 50 wt % to 80 wt % of a beneficial and 20 wt % to 50 wt % of a glyceride in the housing; an expandable member in the housing for pushing the composition from the housing; exit means in the housing for releasing the composition from the delivery system; and wherein the composition is characterized by: the beneficial agent is heated to a temperature approximating its melting temperature before mixing with the glyceride heated to a temperature approximating its melting temperature to provide the composition in the delivery system.

8. The delivery system according to claim 7, wherein the beneficial agent is an ionophore.

9. The delivery system according to claim 7, wherein the beneficial agent comprises a member selected from the group consisting of azolomycin, valinomycin, enniactin, monactin, nonactin, dinactin, trinactin, virginiamycin, tetronasin, rumensin, semduramicin, monesin, nigericin, narasin, salinomycin, isolasalocid, lasalocid, lysocellin, septamycin, laidlomycin, Ionomycin, lenotemycin, grisorixin, ferensimycin, alborixin, rosgramicin, erythromycin, lysocellin, bambermycin, monenomycin, and flavomycin.

10. The delivery system according to claim 7, wherein the glyceride comprises a member selected from the group consisting of a monoglyceride, diglyceride and a triglyceride.

11. The delivery system according to claim 7, wherein the glyceride comprises a saturated fatty acid selected form the group consisting of butyric, isovaleric, caproic, caprylic, capric, lauric, myristic, palmitic, stearic, arachidic, behenic, lignoceric, and certic acid.

12. The delivery system according to claim 7, wherein the glyceride comprises an unsaturated fatty acid selected from the group consisting of decylenic, dodecylenic, palmitoleic, oleic, ricinoleic, petroselinic, vaccenic, linoleic, linolenic, eleostearic, licanic, parinaric, tariric, gadoleic, arachidonic, cetoleic, erucic, and nervonic acid.

13. A process for preparing a composition comprising a beneficial agent and glyceride for addition to a delivery system for use in therapy, wherein the process comprises: first, heating the glyceride to a temperature approximating its melting temperature; second, heating the beneficial agent to a temperature approximating its melting temperature; third, blending into a composition the heated beneficial agent and the heated glyceride; and fourth adding the composition to the delivery system for use in therapy.

14. A composition of matter comprising a beneficial agent and a glyceride, said composition prepared by heating the beneficial agent to its melting temperature, and then blending the heated beneficial agent with the glyceride heated to its melting temperature to provide the composition of matter.

15. A composition of matter comprising 20 to 50 wt % of a glyceride selected from the group consisting of a monoglyceride, diglyceride and triglyceride, and 50 to 80 wt % of a beneficial agent, and wherein the composition is characterized by heating the beneficial agent to its melting temperature prior to its addition to glyceride heated to its melting temperature.

* * * * *